United States Patent
Patel

(10) Patent No.: US 7,476,400 B2
(45) Date of Patent: Jan. 13, 2009

(54) HIGH-CONCENTRATION LIDOCAINE COMPOSITIONS AND METHODS FOR THEIR PREPARATION

(75) Inventor: Pravin M. Patel, Bloomfield Hills, MI (US)

(73) Assignee: Ferndale IP, Inc., Ferndale, MI (US)

( * ) Notice: Subject to any disclaimer, the term of this patent is extended or adjusted under 35 U.S.C. 154(b) by 1263 days.

(21) Appl. No.: 10/290,983

(22) Filed: Nov. 8, 2002

(65) Prior Publication Data

US 2003/0104046 A1 Jun. 5, 2003

Related U.S. Application Data

(60) Provisional application No. 60/338,132, filed on Nov. 13, 2001.

(51) Int. Cl.
*A61K 9/127* (2006.01)
(52) U.S. Cl. ....................... 424/450; 424/489
(58) Field of Classification Search ................ 424/450; 264/4.1, 4.3, 4.6
See application file for complete search history.

(56) References Cited

U.S. PATENT DOCUMENTS

| 4,224,179 | A | * | 9/1980 | Schneider | ................... 264/4.6 |
| 4,235,871 | A | | 11/1980 | Papahadjopoulos et al. | ... 424/19 |
| 4,721,612 | A | | 1/1988 | Janoff et al. | .................. 424/1.1 |
| 4,761,288 | A | * | 8/1988 | Mezei | ......................... 424/450 |
| 4,937,078 | A | * | 6/1990 | Mezei et al. | ................. 424/450 |
| 5,234,767 | A | * | 8/1993 | Wallach | ................... 428/402.2 |
| 5,439,967 | A | * | 8/1995 | Mathur | ....................... 424/450 |
| 5,490,985 | A | * | 2/1996 | Wallach et al. | .............. 424/450 |
| 6,045,824 | A | | 4/2000 | Kim et al. | ................... 424/450 |

* cited by examiner

*Primary Examiner*—Michael G. Hartley
*Assistant Examiner*—Eric E. Silverman

(57) ABSTRACT

A composition comprising lidocaine-containing liposomes wherein the weight concentration of lidocaine in said composition is greater than 10%. The composition is prepared by mixing water with an oil phase comprising lidocaine, a $C_{14}$-$C_{20}$ alcohol, an alkyl ester of a fatty acid, propylene glycol, and a polyalkyl stearate. The non-aqueous phase may also include a phospholipid such as phosphatidyl choline.

20 Claims, No Drawings

HIGH-CONCENTRATION LIDOCAINE COMPOSITIONS AND METHODS FOR THEIR PREPARATION

RELATED APPLICATION

This application claims priority of Provisional Patent Application Ser. No. 60/338,132, filed Nov. 13, 2001, and entitled "High-Concentration Lidocaine Compositions and Methods for Their Preparation."

FIELD OF THE INVENTION

This invention relates generally to compositions for the topical treatment of skin conditions. More specifically, the invention relates to lidocaine containing compositions. Most specifically, the invention relates to lidocaine containing compositions in which the concentration of lidocaine is over 10% by weight and to methods for manufacturing such compositions.

BACKGROUND OF THE INVENTION

Topical anesthetics such as lidocaine, benzocaine and the like are widely used to treat pain and itching associated with insect bites, sunburn, contact dermatitis, and in connection with anal-rectal conditions such as hemorrhoids, fissures and infections. Most preferably, the topical anesthetic material is disposed in a carrier which is a cream, lotion or gel, and in many instances, liposomal structures are particularly favored carriers. As is known in the art, liposomal structures comprise vesicles having walls formed from a phospholipid or similar material.

In general, the efficacy of the anesthetic containing compositions is directly dependent upon the concentration of anesthetic therein. Heretofore, lidocaine containing compositions, particularly those compositions formulated for topical application and/or encapsulated in liposomes, have been restricted to concentrations of approximately 2-5% lidocaine. Such compositions are shown in U.S. Pat. Nos. 4,937,078 and 6,045,824. Prior to the present invention, the art has not been able to prepare stable lidocaine containing preparations which are suitable for topical application to the skin, and in which the concentration of lidocaine is greater than 10%.

As will be explained in detail herein below, the present invention comprises lidocaine compositions having a weight percentage of lidocaine therein of at least 10%. The compositions of the present invention are generally prepared as liposome based compositions in which the lidocaine is disposed in a non-aqueous phase encapsulated within liposomes and wherein the liposomes are disposed in a continuous, aqueous phase. The overall concentration, by weight, of the lidocaine in the compositions is over 10%, and preferably 12% or more by weight. The compositions of the present invention are easy to prepare and stable on storage. Also within the scope of the present invention are methods for the preparation of the compositions.

BRIEF DESCRIPTION OF THE INVENTION

There is disclosed herein a formulation comprising lidocaine-containing liposomes wherein the weight concentration of lidocaine in the formulation is greater than 10%. The formulation is prepared by mixing an aqueous composition and a non-aqueous composition so as to form a liposomal structure. The non-aqueous composition is comprised of lidocaine, a $C_{14}$-$C_{20}$ alcohol, an alkyl ester of a fatty acid, propylene glycol and a polyalkyl stearate. The aqueous composition may comprise water, and may further include coloring agents, fragrances and the like. The non-aqueous composition may further include a phospholipid such as phosphatidyl choline. The non-aqueous composition may further include benzyl alcohol, a polysorbate, vitamin E, cholesterol and/or an emulsifier.

In particular embodiments, the $C_{14}$-$C_{20}$ alcohol comprises a $C_{16}$-$C_{18}$ alcohol such as cetostearyl alcohol. In certain embodiments, the lidocaine comprises, on a weight basis, 20-30% of the non-aqueous phase.

DETAILED DESCRIPTION OF THE INVENTION

In accord with the present invention, high concentration, liposomal preparations of lidocaine and similar topical anesthetic materials are prepared by a method wherein the lidocaine is incorporated into a non-aqueous phase composition; this portion of the formulation is often referred to as the "oil phase." This oil phase is then mixed with an aqueous phase under conditions which cause the formation of liposomes.

The oil phase includes lidocaine, typically at a concentration of 20 to 30% by weight of the oil phase. (All percentages herein, unless otherwise noted, are on the basis of weight.) This phase further includes a solvent material, which comprises an alkyl ester of a fatty acid which most preferably is a $C_1$-$C_4$ ester of a $C_8$-$C_{18}$ acid. One particularly preferred solvent material comprises isopropyl myristate, although it is to be understood that similar materials could likewise be employed. This solvent material typically comprises, by weight, 5 to 20% of the oil phase. The oil phase also includes a $C_{14}$-$C_{20}$ alcohol in a weight percent of approximately 10-30%. This fatty alcohol functions as a viscosity builder. One particularly preferred fatty alcohol is a material known in the art as cetostearyl alcohol, and this material comprises a mixture of $C_{16}$-$C_{18}$ alcohols. The oil phase also includes an emulsion former in an amount of 0.5-5% by weight of the oil phase. One particularly preferred group of emulsion formers comprises polyalkyl stearates. A particularly preferred polyalkyl stearate is a polyoxyethylene derivative of stearic acid, and such materials are commercially available under the designation Myrj from ICI Inc. Equivalent materials may likewise be employed. The oil phase also preferably includes a water miscible solvent such as propylene glycol, typically present in an amount, by weight, of 10 to 30% of the oil phase.

The oil phase preferably includes phospholipids which function to facilitate the creation of the vesicle walls, and one particularly preferred phospholipid comprises phosphatidyl choline, which is available from the American Lecithin Corporation under the designation Phospholipion®. When employed, this material is typically present in an amount of 10-20% by weight of the oil phase. Emulsifiers may also be employed in the formulations of the present invention; and one preferred group of emulsifiers includes polysorbates, which may comprise, by weight, 0.3 to 6% of the oil phase. In some instances, antioxidants such as vitamin E are included in the composition. Cholesterol has also been found to be a beneficial additive, and it is believed to stabilize the liposomal structure. When employed, cholesterol typically comprises 0.1-3% of the oil phase.

In order to prepare the composition of the present invention, the foregoing oil phase ingredients are all blended together, preferably at an elevated temperature so as to facilitate formation of a homogeneous mixture. Typically, the materials are stirred together at a temperature of 80° C. for one-quarter to one-half hour. Most preferably, the lidocaine is added after all of the other ingredients are dissolved.

The aqueous phase of the composition, in its most basic form, comprises water; although, additional ingredients such as coloring agents, fragrances and the like may be added to the water phase. In order to prepare the liposomal structure, roughly equal amounts of the oil phase and water phase material are mixed together, most preferably at a temperature of 60-70° C. This mixture is placed into a homogenizer which may be any homogenizer known and used in the art for the formation of liposomal structures. The mixture is stirred in the homogenizer, typically at speeds in the range of 2000 to 5000 rpm for 5 to 20 minutes, and this procedure produces a creamy material having a liposomal structure in which the lidocaine material is disposed within the liposomes. The overall concentration of the lidocaine in this material will be in the range of 10 to 15% by weight of the total composition, although the method may be adapted for the preparation of higher concentration formulas.

The foregoing lidocaine composition has a uniform, creamy texture suitable for use as a topical treatment. It is significant that this composition is stable on long term storage and does not phase separate or produce crystallization or other degradation of the lidocaine. Heretofore, stable compositions having lidocaine concentrations of greater than 10% have not been achievable.

One specific composition prepared in accord with the present invention comprises, on a weight basis:

2.0% benzyl alcohol NF
5.75% isopropyl myristate NF
0.3% cholesterol UPN
1.0% polyoxyl 40 stearate (Myij)
10.0% cetostearyl alcohol
10.0% propylene glycol UPN
0.3% vitamin E acetate UPN
1.5% polysorbate 80 NF
7.32% Phospholipion® 80 H
12.5% lidocaine
49.33% water The first ten ingredients were used to prepare the oil phase, which was then mixed with the water to form the liposomes. At the time of mixing, the oil phase had a temperature of 68° C. and the water phase a temperature of 68.4° C. Mixing was carried out for 10 minutes, in a Mokon temperature-controlled homogenizer operating at 3396 rpm. Once homogenization is complete, the material is gently mixed for 40 minutes. The foregoing produced a stable liposomal cream composition.

A second specific composition prepared in accord with the present invention comprises, on a weight basis:

2.0% benzyl alcohol NF
5.75% isopropyl myristate NF
0.30% cholesterol UPN
1.0% polyoxyl 40 stearate (Myrj)
7.5% cetostearyl alcohol
10.0% propylene glycol UPN
0.30% vitamin E acetate UPN
1.50% polysorbate 80 NF
7.32% Phospholipion® 80 H
12.5% lidocaine
51.83% purified water As in the previous example, the first ten ingredients were used to prepare the oil phase which was then mixed with the water to form the liposomes as described hereinabove. This procedure produced a stable liposomal cream composition.

Yet other compositions may be prepared in accord with the methods and teaching herein. In that regard, the compositions and specific materials may be varied within the ranges presented herein. Also, while the present invention has been described primarily with reference to the preparation of lidocaine-based compositions, the principles thereof are not limited in this regard, and can be employed for the preparation of compositions including other topical anesthetics such as benzocaine and the like. Yet other modifications and variations of the compositions and methods of the present invention will be readily apparent to one of skill in the art in view of the teaching set forth herein.

It is to be understood that in accord with the principles of the present invention, other similar compositions may be prepared. The foregoing discussion, description and examples are illustrative of specific embodiments of the invention, but are not meant to be limitations upon the practice thereof. It is the following claims, including all equivalents, which define the scope of the invention.

The invention claimed is:

1. A method for preparing a composition comprising topical anesthetic containing liposomes wherein the weight concentration of the topical anesthetic in said composition is greater than 10%, said method comprising:
   providing a non-aqueous composition, said non-aqueous composition comprising:
   a topical anesthetic,
   a $C_{14}$-$C_{20}$ alcohol,
   an alkyl ester of a fatty acid,
   propylene glycol,
   a polyalkyl stearate;
   providing an aqueous composition comprising water; and
   mixing said aqueous composition and said non-aqueous composition so as to form a liposomal structure wherein said liposomes are disposed in said aqueous composition and wherein the concentration of said topical anesthetic in said composition is greater than 10%.

2. The method of claim 1, wherein said topical anesthetic is lidocaine.

3. The method of claim 1, wherein said non-aqueous composition further includes a phospholipid.

4. The method of claim 3, wherein said phospholipid is phosphatidyl choline.

5. The method of claim 1, wherein said non-aqueous composition further includes benzyl alcohol.

6. The method of claim 1, wherein said non-aqueous composition further includes one or more of: a polysorbate, vitamin E, cholesterol, and an emulsifier.

7. The method of claim 1, wherein said $C_{14}$-$C_{20}$ alcohol comprises a $C_{16}$-$C_{18}$ alcohol.

8. The method of claim 1, wherein said $C_{14}$-$C_{20}$ alcohol comprises cetostearyl alcohol.

9. The method of claim 1, wherein said alkyl ester of a fatty acid comprises a $C_1$-$C_4$ ester of a $C_8$-$C_{18}$ fatty acid.

10. The method of claim 8, wherein said alkyl ester of a fatty acid comprises isopropyl myristate.

11. The method of claim 1, wherein said polyalkyl stearate comprises a polyoxyethylene derivative of stearic acid.

12. The method of claim 2, wherein said lidocaine comprises, on a weight basis, 20-30% of said non-aqueous phase.

13. The method of claim 1, wherein said $C_{14}$-$C_{20}$ alcohol comprises, on a weight basis, 10-30% of said non-aqueous phase.

14. The method of claim 1, wherein said alkyl ester of a fatty acid comprises, on a weight basis, 5-15% of said non-aqueous phase.

15. The method of claim 1, wherein said propylene glycol comprises, on a weight basis, 10-30% of said non-aqueous phase.

16. The method of claim 1, wherein said polyalkyl stearate comprises, on a weight basis, 0.5-5% of said non-aqueous composition.

17. The method of claim 3, wherein said phospholipid comprises, on a weight basis, 10-20% of said non-aqueous phase.

18. The method of claim 1, wherein said step of mixing said non-aqueous composition and said aqueous composition comprises mixing equal weight amounts of said aqueous composition and said non-aqueous composition.

19. A composition made according to the method of claim 2.

20. A method of making a composition comprising lidocaine-containing liposomes wherein the weight concentration of lidocaine in said composition is greater than 10%, said method comprising the steps of:

preparing a non-aqueous composition, said non-aqueous composition comprising, on a weight basis, 4% benzyl alcohol, 11.5% isopropyl myristate, 0.6% cholesterol, 2.0% polyoxyethylene stearate, 20% cetostearyl alcohol, 20% propylene glycol, 0.6% vitamin E acetate, 3.0% polysorbate, 14.64% phosphatidyl choline, and 25% lidocaine;

providing an aqueous composition comprising water; and mixing approximately equal weight amounts of said non-aqueous composition and said water, and stirring said composition so as to form said liposomes.

\* \* \* \* \*